United States Patent [19]
Kelly

[11] 4,100,178
[45] Jul. 11, 1978

[54] 4,5-DIDEHYDRO-6-METHOXY-2-ARYLMETHOXYMETHYL-4α-TETRAHYDROPYRANACETIC ACID ALKYL ESTERS

[75] Inventor: Robert C. Kelly, Kalamazoo, Mich.

[73] Assignee: The Upjohn Company, Kalamazoo, Mich.

[21] Appl. No.: 784,178

[22] Filed: Apr. 4, 1977

Related U.S. Application Data

[62] Division of Ser. No. 676,895, Apr. 14, 1976, Pat. No. 4,032,542.

[51] Int. Cl.$^2$ ............................................. C07D 309/22
[52] U.S. Cl. ............................................... 260/345.8 P
[58] Field of Search .......... 260/345.7, 345.8, 345.8 R, 260/345.8 P, 345.7 R, 345.7 P

[56] References Cited

U.S. PATENT DOCUMENTS

| | | | |
|---|---|---|---|
| 4,018,804 | 4/1977 | Schneider | 260/345.8 R |
| 4,020,173 | 4/1977 | Kelly et al. | 260/343 |
| 4,048,194 | 9/1977 | Nelson | 260/345.8 P |

*Primary Examiner*—Nicky Chan
*Attorney, Agent, or Firm*—Robert A. Armitage

[57] ABSTRACT

The present specification provides novel intermediates and novel processes for the synthesis of Thromboxane B$_2$ 11a-homo-11a-oxa-PGF$_{2\alpha}$), its 15-epimer, and various carboxyl derivatives thereof. In particular, there are disclosed various bicyclic tetrahydrofuran-containing lactones useful in the above processes, and corresponding acyclic lactones.

2 Claims, No Drawings

4,5-DIDEHYDRO-6-METHOXY-2-ARYLMETHOXYMETHYL-4α-TETRAHYDROPYRANACETIC ACID ALKYL ESTERS

The present application is a divisional application of Ser. No. 676,895, filed Apr. 14, 1976, now issued as U.S. Pat. No. 4,032,542, on June 28, 1977.

The present invention relates to Thromboxane $B_2$ and associated intermediates and processes, for which the essential material constituting a disclosure therefor is incorporated by reference here from Ser. No. 676,890, filed Apr. 14, 1976, now issued as U.S. Pat. No. 4,020,173 on Apr. 26, 1977.

I claim:

1. A thromboxane intermediate of the formula

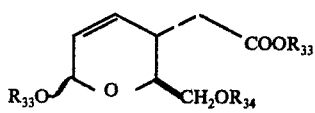

wherein $R_{34}$ is an arylmethyl hydroxy-hydrogen replacing group selected from the group consisting of
   (a) benzyl,
   (b) benzyl substituted by one to five alkyl of one to four carbon atoms, inclusive, chloro, bromo, iodo, fluoro, nitro, phenylalkyl of 7 to 12 carbon atoms, inclusive,
   (c) benzhydryl,
   (d) benzhydryl substituted by one to ten alkyl of one to four carbon atoms, inclusive, chloro, bromo, iodo, fluoro, nitro, phenylalkyl of 7 to 12 carbon atoms, inclusive,
   (e) trityl, and
   (f) trityl substituted by one to 15 alkyl of one to four carbon atoms, inclusive, chloro, bromo, iodo, fluoro, nitro, phenylalkyl of 7 to 12 carbon atoms, inclusive; and wherein $R_{33}$ is alkyl of one to 5 carbon atoms, inclusive.

2. 4,5-Didehydro-6-hydroxy-2β-benzyloxymethyl-3α-tetrahydropyranacetic acid, methyl ester, a compound according to claim 1.

* * * * *

UNITED STATES PATENT AND TRADEMARK OFFICE
CERTIFICATE OF CORRECTION

PATENT NO. : 4,100,178
DATED : July 11, 1978
INVENTOR(S) : Robert C. Kelly

It is certified that error appears in the above-identified patent and that said Letters Patent are hereby corrected as shown below:

Column 2, line 21, "6-hydroxy-" should read -- 6-methoxy- --.

Signed and Sealed this

Twenty-sixth Day of June 1979

[SEAL]

Attest:

RUTH C. MASON
*Attesting Officer*

DONALD W. BANNER
*Commissioner of Patents and Trademarks*